United States Patent [19]
Crawley et al.

[11] 3,966,756
[45] June 29, 1976

[54] SUBSTITUTED DIBENZO[b,f]TETRAZOLO[1,5-d][1,4]-OXAZEPINES

[75] Inventors: Lantz Stephen Crawley, Spring Valley, N.Y.; Sidney Robert Safir, River Edge, N.J.

[73] Assignee: American Cyanamid Company, Stamford, Conn.

[22] Filed: Apr. 7, 1975

[21] Appl. No.: 565,907

[52] U.S. Cl. .............................. 260/308 D; 424/269
[51] Int. Cl.² ........................................ C07D 257/04
[58] Field of Search ................................ 260/308 D

[56] References Cited
FOREIGN PATENTS OR APPLICATIONS

| | | | |
|---|---|---|---|
| 350,782 | 6/1931 | United Kingdom | 260/308 D |
| 1,185,539 | 3/1970 | United Kingdom | 260/308 D |

*Primary Examiner*—Frederick E. Waddell
*Attorney, Agent, or Firm*—Denis A. Polyn

[57] ABSTRACT

12-Substituted dibenzo[b,f]tetrazolo[1,5-d] [1,4]oxazepines and method of preparation are described. They are useful for their analgesic activity.

4 Claims, No Drawings

SUBSTITUTED DIBENZO[B,F]TETRAZOLO[1,5-D][1,4]-OXAZEPINES

DESCRIPTION OF THE INVENTION

This invention is concerned with 12-substituted dibenzo[b,f]tetrazole[1,5-d][1,4]oxazepines which may be illustrated by the following formula:

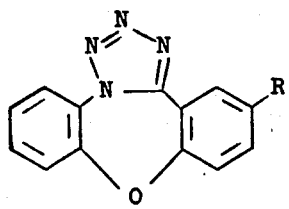

wherein R is selected from the group comprising hydrogen and halogen. Halogen is defined as chlorine, bromine, iodine or fluorine.

The compounds of the present invention may be prepared according to the following reaction sequence:

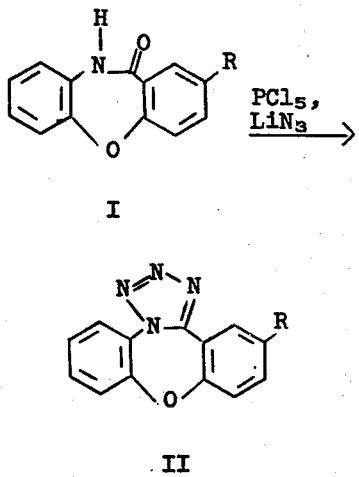

A lactam (I) and phosphorus pentachloride are suspended in anhydrous toluene and heated at reflux under nitrogen. The solvent is removed under reduced pressure. More toluene is introduced and again removed. The residue, dissolved in dimethylformamide is added dropwise to a suspension containing sodium azide and lithium chloride in dimethylformamide. The reaction mixture is heated at about 100°C for several hours, cooled and poured into water. The resulting precipitate is removed by filtration and air dried. The product (II) may be recrystallized from alkanols.

Compounds within the scope of the present invention are for example:
12-Chloro-dibenzo[b,f]tetrazolo[1,5-d][1,4]oxazepine
Dibenzo[b,f]tetrazolo[1,5-d][1,4]oxazepine
12-Fluoro-dibenzo[b,f]tetrazolo[1,5-d][1,4]oxazepine
12-Bromo-dibenzo[b,f]tetrazolo[1,5-d][1,4]oxazepine The compounds of the present invention exhibit analgesic acitivity when measured by a modification of the method of Randall and Selitto, Arch. Int. Pharmacodyn., III, 409 (1957). This test measures the pain threshold of rats whose paws are made sensitive to pressure by the injection of 0.1 ml. of a 20% aqueous suspension of brewers' yeast into the plantar surface of the left hind paw. Constantly increasing force (16 g./sec.) is applied to the swolled paw using an Analgesy Meter, Ugo Basile. The pressure is cut off at 250 g. of force when there is no response (sudden struggle or vocalization). Control rats treated with starch vehicle respond to a pressure of about 30 g. Pressure-pain thresholds are always recorded 2 hours after administration of brewers' yeast. Test compounds are administered at the same time as the yeast, at an oral dose of 200 mg./kg. Ratios of treated (T) over control (C) reaction thresholds are calculated as estimates of analgesic efficacy (degree of analgesia obtainable). Test compounds are accepted as active when they produce a 100% elevation of pain threshold (T/C ≧ 1.37). The results of this test on representative compounds of this invention appear in Table I.

Table I

| Compound | Ratio T/C |
| --- | --- |
| 12-Chloro-dibenzo[b,f]tetrazolo-[1,5-d][1,4]oxazepine | 2.72 |
| Dibenzo[b,f]tetrazolo[1,5-d][1,4]-oxazepine | 1.58 |

The compounds of the present invention are active analgesics when measured by the "writhing syndrome" test as described by Siegmund, et al., Proc. Soc. Exp. Bio. and Med., 95, 729 (1957) with modifications. This method is based upon the reduction of the number of writhes following the intraperitoneal injection of one mg./kg. of body weight of phenyl p-quinone in male Swiss albino mice weighing 15–25 g. The syndrome is characterized by intermittent contractions of the abdomen, twisting and turning of the trunk and extension of the hind legs, beginning 3 to 5 minutes after injection of the phenyl p-quinone. The test compounds are administered orally at the indicated dose to groups of 2 mice each, 30 minutes before injection of the phenyl p-quinone. The total number of writhes exhibited by each group of mice is recorded for a three minute period, commencing 15 minutes after injection of the phenyl p-quinone. A compound is considered active if it reduces the total number of writhes in 2 test mice from a control value of approximately 30 per pair to a value of 18 or less. Table II summarizes the results of this test on a representative compound of this invention.

Table II

| Compound | Dose mg/kg | No. of writhes per pair |
| --- | --- | --- |
| 12-Chloro-dibenzo[b,f]-tetrazolo [1,5-d][1,4]-oxazepine | 100 | 7, 9 |

The compounds of the present invention exhibit analgesic activity when measured by a modification of the method of Gray, Osterberg and Scuto, J. Pharmacol. Exp. Ther. 172, 154–162 (1970).

Voltage to a lamp is varied to produce three graded intensities of stimuli and reaction times, arbitrarily labeled low, medium and high. The voltages selected by Variac settings cause control (vehicle treated) rats to react (tail flick) in 18, 12 and 7.9 seconds. The low intensity stimulus was discontinued after 30 seconds if the rat did not respond. The cutoff times for the medium and high intensity stimuli were 25 and 15 seconds respectively. Reaction time was measured to the nearest 0.1 second by an electric stopwatch synchronized with the lamp. The compounds were administered orally at the indicated doses to groups of 6 male Wistar strain rats weighing 125 to 160 g. Control rats received the vehicle alone. Beginning 60 minutes later and during the period of peak effect reaction times were determined. The order of testing each rat from low to high stimulus intensity was varied in replicate experiments with an interval of about 15 minutes between each measurement of reaction time.

The measure of analgesia was the weighted ratio of treated (T) to control (C) reaction times calculated by the statistical method of Cohen. A compound is considered active when two positive results are achieved in two different experiments. The results appear in Table III.

Table III

| Compound | Dose mg/kg | T/C Ratio* |
|---|---|---|
| 12-Chloro-dibenzo[b,f]tetrazolo[1,5-d][1,4]oxazepine | 200 | 19.46 |
| Dibenzo[b,f]tetrazolo[1,5-d][1,4]oxazepine | 200 | 27.18 |

*Compounds are considered active if the T/C ratio is greater than or equal to 17.79.

The active components of this invention may be used in conventional pharmaceutical dosage forms such as tablets, capsules, elixirs, emulsions, syrups, sustained release preparations and the like, which may contain the usually accepted pharmaceutical excipients.

Example 1

Preparation of 12-Chloro-dibenzo[b,f]tetrazolo[1,5-d][1,4]oxazepine

A 2.45 g. portion of 12-chloro-dibenz[b,f][1,4]oxazepin-11(10H)-one (prepared as described in U.S. Patent 3,337,536) and 2.28 g. of phosphorus pentachloride are placed in 20 ml. of toluene and heated at reflux for 4 hours. The solvent is removed under reduced pressure and then 10 ml. of toluene is added and removed to insure removal of HCl and phosphorus oxychloride. The residue is dissolved in 20 ml. of dimethylformamide and added dropwise with stirring to a suspension prepared by adding 1.30 g. of sodium azide and 0.84 g. of lithium chloride to 25 ml. of dimethylformamide. The reaction is heated at 100°C. overnight and then cooled. The addition of water causes a yellow precipitate which is collected by filtration, washed with water, dried and recrysstallized from 10:1 ether:ethyl acetate, m.p. 209°–211°C.

EXAMPLE 2

Preparation of Dibenzo[b,f]tetrazolo[1,5-d][1,4]oxazepine

A 2.11 g. portion of dibenz[b,f][1,4]oxazepin-11(10H)-one (prepared as described in U.S. Pat. No. 3,337,536) and 2.28 g. of phosphorus pentachloride are placed in 20 ml. of toluene and reacted as described in Example 1. The reaction gives a dark oil. The addition of water gives a bulky tan precipitate which after recrystallization from methanol has a m.p. 206°-208°C.

EXAMPLE 3

Preparation of 12-Fluoro-dibenzo[b,f]tetrazolo[1,5-d][1,4]oxazepine

A 45 g. portion of 2-(p-fluorophenoxy)aniline in 300 ml. of ether is added slowly to a solution of 55 g. of phosgene in 100 ml. of ether and 250 ml. of dichlorobenzene at −10°C. with stirring. The reaction is stirred for 1 hour at −10°C. and then heated slowly with stirring to 160°C. The solution is cooled to 120°C. and added to a pre-heated solution of 80 g. of aluminum chloride in 400 ml. of dichlorobenzene. The reaction is heated to 180°C. for one hour, cooled to 75°C. and poured into a mixture of 400 g. of ice and 500 ml. of water with stirring. The solution is heated to 100°C. and allowed to cool and stand for 2 days at room temperature. A 600 ml. portion of petroleum ether is added and the mixture is stirred to break up the emulsion. The solid is filtered, washed with 300 ml. of petroleum ether and 600 ml. of water and dried at 75°C., m.p. 235°–237°C. This product is 12-fluoro-dibenz[b,f][1,4]oxazepin-11(10H)-one.

A 2.29 g. portion of 12-fluoro-dibenz[b,f][1,4]oxazepin-11(10H)-one and 2.28 g. of phosphorus pentachloride are placed in 20 ml. of toluene and reacted as described in Example 1. The reaction gives a tan solid which is recrystallized from methanol, m.p. 185°–186°C.

We claim:
1. A compound of the formula:

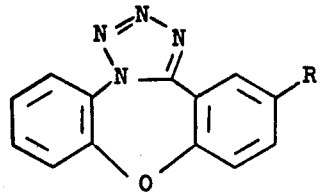

wherein R is selected from the group consisting of hydrogen and halogen.

2. The compound according to Claim 1 wherein R is chloro.

3. The compound according to Claim 1 wherein R is hydrogen.

4. The compound according to Claim 1 wherein R is fluoro.

* * * * *